United States Patent [19]

Cook et al.

[11] Patent Number: 5,723,151
[45] Date of Patent: Mar. 3, 1998

[54] CELLULOSE ACETATE PHTHALATE ENTERIC COATING COMPOSITIONS

[75] Inventors: Phillip Michael Cook, Kingsport, Tenn.; Michael Wayne Adams, Raleigh, N.C.; Joseph Vaden Smith, Kingsport, Tenn.

[73] Assignee: Eastman Chemical Company, Kingsport, Tenn.

[21] Appl. No.: 554,020

[22] Filed: Nov. 6, 1995

[51] Int. Cl.$^6$ .................................................. A61K 9/20
[52] U.S. Cl. .................. 424/459; 424/464; 424/480; 424/482; 424/494; 424/495; 536/64; 525/54.21; 527/311
[58] Field of Search ............................. 424/459, 464, 424/480, 482, 494, 495; 536/64; 525/54.21; 527/311

[56] References Cited

U.S. PATENT DOCUMENTS

| | | | |
|---|---|---|---|
| 2,196,768 | 4/1940 | Hiatt | 167/82 |
| 2,856,400 | 10/1958 | Malm et al. | 260/225 |
| 3,391,135 | 7/1968 | Ouno et al. | 260/214 |
| 3,505,312 | 4/1970 | Malm et al. | 260/225 |
| 3,629,237 | 12/1971 | Koyanagi et al. | 260/226 |
| 3,789,117 | 1/1974 | Tsujino | 424/35 |
| 4,960,814 | 10/1990 | Wu et al. | 524/312 |
| 5,356,634 | 10/1994 | Wu et al. | 424/464 |

FOREIGN PATENT DOCUMENTS

| | | | |
|---|---|---|---|
| 879813 | 8/1971 | Canada | 536/64 |
| 1155500 | 5/1968 | United Kingdom . | |

OTHER PUBLICATIONS

*Handbook of Pharmaceutical Excipients*, American Pharmaceutical Association, et al, Washington XP002027710 153140, pp. 51–52, (1988).

Kirk–Othmer, Encyclopedia of Chemical Technology, Third Edition, vol. 5, pp. 118–143 (1979), John Wiley & Sons, NY, N.Y.

Encyclopedia of Polymer Science and Engineering, vol. 3, pp. 158–181 (1985), John Wiley & Sons, Ny, N.Y.

Ullman's Encyclopedia of Industrial Chemistry, Fifth Completely Revised Edition, vol. A5, pp. 438–447 (1986) VCH Verlagsgesellschaft, Weinheim, Germany.

*Primary Examiner*—Frederick Krass
*Attorney, Agent, or Firm*—Bernard J. Graves, Jr.; Rose M. Allen; Harry J. Gwinnell

[57] ABSTRACT

Provided are enteric coating compositions which utilize a low viscosity cellulose acetate phthalate polymer as a film former. The cellulose acetate phthalates have an inherent viscosity of about 0.2 to 0.6 dL/g and phthalyl values of from 30 to 40% and can be applied to solid oral medicaments with less solvent than conventional cellulose acetate phthalate polymers. Also provided is a process for preparing the low viscosity cellulose acetate phthalate polymers.

9 Claims, No Drawings

CELLULOSE ACETATE PHTHALATE ENTERIC COATING COMPOSITIONS

FIELD OF THE INVENTION

This invention relates to enteric coating compositions for oral medicaments. In particular, it relates to polymers useful in enteric coating compositions.

BACKGROUND OF THE INVENTION

It is often desirable to coat tablets of pharmaceutical products with a material which prohibits release of the active ingredient in the low pH medium of the stomach but enables rapid release in the higher pH medium of the upper small intestine. Such coatings are commonly referred to as enteric coatings. They are useful in protecting the active ingredient in the formulation from hydrolysis or degradation in the stomach and in preventing the release in the stomach of ingredients which can cause nausea or other undesirable pharmacological effects. The rapid dissolution at higher pH ensures that all of the active ingredient is released in the upper part of the intestine. Hydroxypropyl methylcellulose phthalate and cellulose acetate phthalate are two principal polymers used in enteric coatings.

U.S. Pat. No. 3,391,135 describes a process for preparing low molecular weight cellulose derivatives, wherein 2% by weight of such derivatives should exhibit a solution viscosity of less than 10 cps at 20° C. This reference teaches cellulose acetate, cellulose butyrate, and cellulose phthalate. We have found that cellulose acetate phthalate with a solution viscosity as low as taught in this reference produces unacceptably poor enteric coatings.

U.S. Pat. No. 5,356,634 describes compositions comprised of a cellulose acetate phthalate polymer having phthalyl values from 15 to 25%, an inherent viscosity of about 0.3 to 1.0 dL/g, and a molecular weight of about 15,000 to 75,000, and a cellulose acetate trimellitate polymer having trimellityl values of from 15–27%. The cellulose acetate phthalate polymer described in this reference swells to form a sponge-like non-dissolving matrix for sustained-release applications under the basic conditions of the small intestine and thus by design does not fully dissolve; this feature renders such polymers inappropriate for true enteric coating applications where it is desireable to have the coating dissolve fully under the basic conditions of the small intestine to allow complete and immediate delivery of the drug dosage.

U.S. Pat. No. 4,960,814 describes water dispersible polymeric compositions based on polymers such as cellulose acetate phthalate. Such compositions are generally deficient due to hyrdolytic instability of the phthalate esters.

U.S. Pat. No. 3,629,237 describes the use of alkali metal salts of oxyacids of halogens to prepare low-viscosity acid phthalates of cellulose ethers. While this reference teaches the inherent viscosity-reduction of cellulose ethers, we have found that alkali metal salts of haloacids such as sodium chlorate are ineffective in reducing the inherent viscosity of many cellulose esters and ethers, while being effective at reducing the inherent viscosity of cellulose acetate phthalate by approximately a factor of 2.7. (See Table VI, below.)

Kirk-Othmer, Encyclopedia of Chemical Technology, Third Edition, Volume 5, pp. 118–143 (1979), John Wiley and Sons, New York, N.Y.; Encyclopedia of Polymer Science and Engineering, Volume 3, pp 158–181 (1985) John Wiley and Sons, New York, N.Y.; and Ullman's Encyclopedia of Industrial Chemistry, Fifth Completely Revised Edition, Volume A5, pp 438–447 (1986) VCH Verlagsgesellschaft, Weinheim, Germany, provide general background information on cellulose ester technology.

Although cellulose acetate phthalate is widely used as the polymer of choice for enteric coatings, the use of cellulose acetate phthalate dissolved in organic solvents has raised some concerns. Increased environmental, health, and safety concerns have forced many manufacturers to reevaluate operations that utilize organic solvents.

SUMMARY OF THE INVENTION

The present invention provides enteric coating compositions comprised of cellulose acetate phthalate having an inherent viscosity of 0.2 to 0.6 dL/g, measured at 25° C. in a (60/40 by weight) mixture of phenol/tetrachloroethane at a concentration of 0.5 g/100 ml, and a phthalyl value of 30 to 40%. The compositions of this invention can be applied to medicaments while using up to about 33% less solvent than conventional cellulose acetate phthalate compositions, while at the same time being capable of application in up to about 27% less time.

The use of the cellulose acetate phthalate formulations of this invention provides the advantages of less solvent recovery and higher solids application than the current commercial solvent based systems, while also enabling the manufacturer to continue using existing equipment.

This invention also provides a process for preparation of low-viscosity cellulose acetate phthalate. Cellulose acetate phthalate can be prepared commercially by reacting cellulose acetate with phthalic anhydride and is used primarily in enteric coating applications. The phthalyl content generally must be in the range of 30–36 wt %. We have found that the solution viscosity of the final product is a function of the degree of phthalyl substitution in the cellulose acetate phthalate product and the inherent viscosity of the starting cellulose acetate raw material. The end use of the product thus fixes the acceptable phthalyl substitution for use as an enteric coating. The inherent viscosity of the product from the current commercial process therefore is fixed by the phthalyl substitution and the inherent viscosity of the cellulose acetate starting material.

One object of this invention is to provide a process by which cellulose acetate phthalate inherent viscosity can be reduced, thereby providing a range of product viscosities independent of the degree of phthalyl substitution or of the viscosity of the cellulose acetate starting material. This viscosity reduction can be accomplished by treating a solution of the higher viscosity cellulose acetate phthalate with an alkali metal salt of a halo acid.

DETAILED DESCRIPTION OF THE INVENTION

The present invention provides an enteric coating composition comprising (a) cellulose acetate phthalate having an inherent viscosity of about 0.2 to 0.6 dL/g, measured at 25° C. in a (60/40 by weight) mixture of phenol/tetrachloroethane at a concentration of 0.5 g/100 mL, and having phthalyl values of 30 to 40%; and (b) an organic solvent.

In a preferred embodiment of the present invention, the cellulose acetate phthalate will have phthalyl values in the range of 30 to 35%.

A preferred inherent viscosity is 0.3 to 0.48 dL/g; most preferred is 0.35 to 0.45 dL/g.

In a further preferred embodiment of the present invention, the enteric composition will utilize the above cellulose acetate phthalate as a film former in the enteric coating composition to the exclusion of other cellulose esters.

Exemplary organic solvents useful in the practice of the present invention include ketones, ethers, esters, and chlorinated hydrocarbons. Examples of such solvents include acetone, 2-butanone, 2-pentanone, ethyl acetate, propyl acetate, propyl ether, tetrahydrofuran, methylene chloride, chlorobenzene, dichlorobenzene, and the like.

The enteric coating compositions of the present invention may further comprise up to about 25 weight percent of at least one coating additive such as pigments, colorants stabilizers, antioxidants, waxes and the like as desired, preferably about 10 to 25 weight percent, based on the total weight of the composition.

Commonly used coating additives include plasticizers such as dimethyl phthalate, diethyl phthalate, dioctyl phthalate, a monoglyceride, or triacetin; water-soluble polymers; annealing agents; pharmaceutical clays; colorants; additional surfactants such as TWEEN 80; thickening agents; and the like.

If the coating polymers exhibit acidic or basic functional groups, it is especially preferred to add a small amount of bases or acids, appropriately, as annealing agents to the coating dopes to partially neutralize the respective coating polymers, while still maintaining the integrity of the composition, so as to enhance the coalescing effect in the film-forming process on the surface of a substrate. A preferred amount of base is about 5% to about 50% equivalent of acid functional groups and a preferred amount of acid is about 5% to about 50% equivalent of basic functional groups. Typical bases included hydroxides such as $NH_4OH$, NaOH, and KOH; typical acids include acetic acid and hydrochloric acid.

Thus, as a further preferred aspect of the present invention, there is provided an enteric coating composition consisting essentially of (a) cellulose acetate phthalate having an inherent viscosity of about 0.2 to 0.6 dL/g, measured at 25° C. in a (60/40 by weight) mixture of phenol/tetrachloroethane at a concentration of 0.5 g/100 mL, and having a phthalyl value of 30 to 40%;

(b) an organic solvent; and (c) one or more additives selected from the group consisting of plasticizers; annealing agents, pharmaceutical clays; surfactants; and thickening agents.

Typical active ingredients include but are not limited to typical medicaments used in the art, such as adrenal cortical steroid inhibitors, analgesics (including aspirin, acetominophen, ibuprofen, codeine, morphine, and opium derivatives and other morphinans), anorexics (including amphetamine and non-amphetamine preparations), anti-alcohol preparations, antiarthritics (including anti-gout preparations), antiinfective drugs (i.e., erythromycin, cephalexin, cefaclor, ampicillin, amoxacillin, and the like), antiviral agents, anti-protozoal agents, anthelmintic agents, adrenergic blocking drugs including alpha- and beta-blocking agents, and the like.

The compositions of the present invention can be used to coat such active ingredients, preferably in tablet form, by methodology known in the art. Typical coating methods for applying enteric polymers are fluidized bed and side vented pan coating processes. In these processes, a coating formulation containing the enteric polymer and possibly other materials such as plasticizers and fillers are applied via spray nozzles onto the active ingredient. The active ingredient, usually in a tablet or bead form, is fluidized with heated gas or agitated by a rotating pan with heated gas while applying the coating to prevent agglomeration and in order to dry the polymer film. Both processes result in a uniform film being applied to the surface of the active ingredient. The release of the active ingredient is controlled by the coating thickness, additives in the coating, and the solubility of the active ingredient.

Thus, as a further aspect of the present invention, there is provided an active ingredient or medicament in granular or tabletted form, coated with the compositions of the present invention.

As a further aspect of the present invention, there is provided a method for treating an animal in need of such treatment comprising administering to said animal a biologically-effective amount of a composition comprising an active ingredient in tablet or granular form, coated with an enteric coating composition of the present invention.

In the method for treating animals, the solid dosage form is preferably administered orally. The solid dosage form contains an effective amount of medicament which is that amount typically used in the art to render a desired treatment. This amount will vary greatly depending upon the nature of the medicament and the desired type of treatment. "Treatment" refers to any desired purpose for administering a medicament such as prevention, control, or cure of a disease; maintaining or improving the health of an animal; increasing weight gain or feed conversion of a farm animal; and the like.

The present commercial grade of cellulose acetate phthalate used in enteric coatings has an inherent viscosity of about 0.68 dL/g. Table I shows the inherent viscosity/molecular weight relationship for several cellulose acetate phthalate samples.

TABLE I

| Inherent Viscosity and Molecular Weight | | |
|---|---|---|
| C-A-P I.V. (dL/g) | $MW_w^1$ × 1000 | $MW_n^2$ × 1000 |
| 0.17 | 8.7 | 4.4 |
| 0.30 | 20.0 | 6.7 |
| 0.34 | 26.0 | 11.0 |
| 0.37 | 27.2 | 11.8 |
| 0.42 | 34.6 | 12.6 |
| 0.44 | 35.0 | 13.0 |
| 0.48 | 35.8 | 14.6 |
| 0.50 | 38.7 | 14.4 |
| 0.52 | 42.0 | 14.0 |
| 0.55 | 45.1 | 17.4 |
| 0.70 | 51.2 | 16.8 |
| 0.68 (commercial) | 65.9 | 19.2 |

*Mol. weights were determined by gel permeation chromatography using the polystyrene equivalent method.
1. Weight Average Molecular Weight.
2. Number Average Molecular Weight.

Table II shows the solution and application conditions for cellulose acetate pthalate solutions with I.V.'s ranging from 0.22 to 0.68 dL/g. The last column in this table gives a visual evaluation of the coatings.

All the solutions were prepared to a solution viscosity of 27.5±1 cps. This allowed the comparison to the control solution (I.V.=0.68 dL/g) which could be considered a typical commercial formulation.

TABLE II

Solution and Application Conditions

| Inherent Viscosity (I.V.dL/g) | Solution Viscosity (cps) | Solution Solids (weight %) | Spray Time (min) | Solution Sprayed (grams) | Coating Weight (%) | Coating Appearance |
|---|---|---|---|---|---|---|
| 0.22 | 26.5 | 20.8 | 7 | 154 | 6.7 | cracks |
| 0.34 | 26.0 | 17.5 | 9 | 183 | 9.5 | cracks |
| 0.37 | 26.5 | 14.5 | 11 | 200 | 10.0 | cracks |
| 0.41 | 27.5 | 14.0 | 11 | 237 | 11.2 | OK |
| 0.52 | 28.0 | 13.0 | 12 | 272 | 10.1 | OK |
| 0.55 | 26.5 | 13.0 | 13 | 246 | 9.0 | OK |
| 0.60 | 28.5 | 9.9 | 15 | 331 | 12.5 | OK |
| 0.68 | 27.5 | 9.8 | 15 | 328 | 9.5 | OK |

Composition and physical properties of the tablets are shown in Table III. These tablets are judged to be representative of commercially produced tablets.

TABLE III

Tablet Core Formulation

| Component | % |
|---|---|
| Diclofenac sodium | 12.5 |
| Microcrystalline Cellulose (Avicel) | 40 |
| Ac-Di-Sol | 10 |
| Fumed silica (Syloid) | 1 |
| MYVATEX TL (Eastman Chemical Company) | 1.5 |
| CA 398-10 (Eastman Chemical Company) | 35 |
| Average tablet weight | 177 mg |
| Tablet diameter | ¼" |
| Tablet hardness | 257 N |

Coating application parameters are shown in Table IV.

TABLE IV

Application Parameters

| Equipment | STREA-1 with Wurster insert |
|---|---|
| Column height | 2" |
| Atomization pressure | 4 bar |
| Bed resistance | 80 |
| Inlet temperature | 35–43° C. |
| Outlet temperature | 31–32° C. |
| Spray rate | 22 mL/min |
| Spray time | 7–15 minutes |

Table V shows how the savings afforded by use of lower (0.41 dL/g) I.V. C-A-P were calculated.

TABLE V

Comparison of Coating Results With 0.68 I.V. and 0.41 I.V. Cellulose Acetate Phthalate

| 1 I.V.(dL/g) | 2 Solution Viscosity (cps) | 3 Weight % Solids | 4 Spray Rate (g./min.) | 5 Spray Time (min.) | 6 Amount of Solid Coated (g.) | 7 Solvent Emitted per 1 kg of Tablets (g.) |
|---|---|---|---|---|---|---|
| 0.68 | 27.5 | 9.8 | 22.1 | 15 | 32.8 | 993 |
| 0.41 | 27.5 | 14 | 21.6 | 11 | 33.2 | 680 |

These results show that use of 0.41 dL/g I.V. cellulose acetate phthalate can be expected to enable a decrease in solvent usage of 32.5% (993-680/15) and a decrease in spray time of 26.7% 15-11/15) to give, as shown by laboratory tests of enteric coating properties, tablets of comparable utility.

We have also discovered a facile process for the preparation of low-viscosity cellulose acetate pthalate. The process comprises addition of an alkali metal salt of an oxyacid of a halogen to the reaction dope during preparation of the cellulose acetate phthalate, or alternatively to a solution of the cellulose acetate phthalate itself.

Thus, the present invention provides a process for reducing the inherent viscosity of cellulose acetate phthalate, which comprises treating a solution of cellulose acetate phthalate with an alkali metal salt of a haloacid.

As a further aspect of the present invention, there is provided a process for preparing a cellulose acetate phthalate having an inherent viscosity of about 0.2 dL/g to about 0.6 dL/g, which comprises dissolving cellulose acetate phthalate in an organic acid, at a temperature of about 60° C. to about 100° C., for a sufficient period of time to afford a cellulose acetate phthalate having an inherent viscosity of about 0.2 to about 0.6 dL/g.

As noted above, the low viscosity cellulose acetate phthalates can also be produced using the alkali metal salts of haloacids in the reaction which forms the cellulose acetate phthalate. Accordingly, as a further aspect of the invention, there is provided a process for preparing a cellulose acetate phthalate having an inherent viscosity of about 0.2 dL/g to about 0.6 dL/g, which comprises treating a solution of cellulose acetate with phthalic anhydride and an alkali metal salt of a halo acid.

Because of cost and availability, the salt of choice is sodium chlorate, but others such as potassium chlorate, potassium bromate, sodium bromate, and the like may be also be used. The alkali metal salt may be added to the reaction mixture at any point during the reaction or it may be added after the phthalation is complete. Alternatively, the cellulose acetate phthalate may be prepared and isolated using procedures well known in the art without achieving this inherent viscosity reduction and then redissolved for the viscosity-reduction process. The amount of salt added depends on the amount of viscosity reduction desired, but is preferably less than 4% of the total solution weight. Additions of greater than 4% of the salt are relatively ineffective because of the limited solubility of the salt in acetic acid or in the reaction mixture. The viscosity reduction is preferably accomplished at temperatures of 60°–100° C. or more preferably 70°–90° C. over time periods of 1 to 8 hours but more preferably 2 to 5 hours. Reaction time may be extended still further but we have found no direct benefit to increasing the reaction time on the quality of the final product. The extent of viscosity reduction was found to increase with increasing reaction temperature, increasing reaction time and increasing alkali metal salt concentration.

This invention enables the manufacture of a wide range of product viscosities from a single cellulose acetate starting material. For example, a typical commercial cellulose acetate phthalate product has an inherent viscosity of 0.68 dL/g. A product having the same phthalyl content as that of the current commercial product and a reduced inherent viscosity (see Experimental Section) of 0.42 dL/g can be prepared from the same cellulose ester starting material by application of the methodology of our invention.

One advantage of the lower inherent viscosity product prepared utilizing the methodology of our invention is that enteric coating may be applied at higher solids concentration. The use of higher solids in the enteric coating process reduces coating application costs, reduces organic emissions to the environment, and potentially expands the market for cellulose acetate phthalate.

It is surprising that alkali metal salts of the type employed in this invention would reduce the viscosity of cellulose acetate phthalate. Although the use of such salts can reduce the viscosity of certain cellulose ethers as taught in U.S. Pat. No. 3,629,237, the reduction is not observed for many cellulose esters nor for all cellulose ethers. For example, we have demonstrated that the viscosity reduction methodology does not work for cellulose acetate, cellulose acetate succinate, cellulose acetate hexahydrophthalate and for cellulose ethers, such as methylcellulose, ethylcellulose and hydroxypropyl methylcellulose (see Table VI below).

The cellulose acetate phthalate (low viscosity) samples with different inherent viscosities are listed in Table I. The powders were dissolved in a 1:1 by weight acetone/ethanol mixture and plasticized with diethyl phthalate (DEP). The DEP concentration was equal to 25% of the dry polymer weight in each case. The cellulose acetate phthalate (0.68 dL/g) control solution was prepared initially to determine a reference viscosity for the remaining samples. Each sample was prepared in precisely the same manner as the control solution. Viscosities were determined using a Brookfield Viscometer equipped with a #2 spindle adjusted to a speed of 100. The solutions were applied to diclofenac sodium tablets (Table II) using the STREA-1 bench-top laboratory air suspension coater (Table III). All solutions were sprayed using analogous parameters except for the spray time which was directly proportional to the amount of solution sprayed. The coated tablets were placed in open pans which were placed in a laboratory hood to allow thorough drying of the tablet coating. The tablets were examined daily for defects. On the third day, hairline cracks were observed in formulations using 0.22, 0.34, and 0.37 I.V. cellulose acetate phthalate. Tablets from all eight formulations were examined under the microscope, but no additional defects were observed. The magnitude of fractures decreased with increasing I.V. The enteric properties of the tablets were tested twenty-four hours after coating using a modified USP disintegration procedure. The tablets were first placed in simulated gastric fluid (SGF) with a pH of 1.2 where they remained for a period of 1-hour. The tablets were then removed, examined for coating failures, and placed in simulated intestinal fluid of pH 6.8 where time to disintegration was monitored.

The inherent viscosities of the polymers were determined in 60/40 (wt/wt) phenol/tetrachloroethane at a temperature of 25° C. and a concentration of 0.5 g/100 mL using a calibrated Ubbelohde viscometer at 25° C.

The following general procedure was used to investigate the effect of sodium chlorate on inherent viscosity reduction of several cellulose esters and ethers:

In a three-necked, round-bottomed flask equipped with a mechanical stirrer, thermometer, condenser, and blanketed with nitrogen, were placed 300 grams of acetic acid and 100 grams of the cellulose ester or cellulose ether. The materials were heated at 75° to 80° C. until the cellulose component dissolved. Then 5 grams of sodium chlorate was added and the reaction mixture was stirred for 7 hours at 75° to 80° C. The product was isolated by diluting the reaction mixture with 300 grams of acetic acid. The diluted reaction mixture was then added to one-liter of vigorously stirred water at 5°–50° C. As the reaction mixture was added to the water, the cellulose ester or ether precipitated. For those cellulose ethers soluble in water, isopropyl alcohol was used to precipitate the product. The water slurry of cellulose ester or alcohol slurry of cellulose ether was then filtered and washed with water or isopropyl alcohol. The product was dried in a forced air oven for 24 hours at 60° to 65° C. The table listed below gives the inherent viscosities before and after exposure to sodium chlorate in acetic acid at 75°–80° C.

TABLE VI

Effect of Sodium Chlorate on the Inherent Viscosity of Various Cellulose Esters and Ethers

| Cellulose Component | Reaction Product Inherent Viscosity, dL/g | |
|---|---|---|
| | Before | After |
| Cellulose Acetate Phthalate* | 0.64 | 0.24 |
| Cellulose Acetate Hexahydrophthalate | 0.52 | 0.49 |
| Cellulose Acetate Succinate | 0.82 | 0.80 |
| Cellulose Acetate 398-10* | 1.10 | 1.08 |
| Ethyl Cellulose** | 0.80 | 0.79 |
| Hydroxypropyl methylcellulose** | 1.74 | 1.75 |

*Available from Eastman Chemical Company Kingsport, TN
**Available from Dow Chemical Company Midland, MI The following examples represent pilot plant scale practice of the invention.

Preparation of Typical Commercial Cellulose Acetate Phthalate

EXAMPLE 1

This example does not utilize the viscosity-reduction methodology. To a 5-gallon sigma-blade mixer is added 3583 g acetic acid, 3344 g cellulose acetate having a 32.0% acetyl content and a 232 cp viscosity (10% solution in pyridine at 25° C.), 145 g sodium acetate, and sufficient water to bring the total water content, including that in the cellulose acetate, to 209 g. The batch is then agitated for 4 hours at 73° C. to dissolve the cellulose acetate. To the mixer is then added 3780 g phthalic anhydride and 1308 g sodium acetate. After adjusting the batch temperature to 83° C., 1308 g of acetic anhydride is added to the mixer and the batch is reacted for 4 hours at 82° C. The product is isolated by precipitation into water and dried to less than 2% water content in a fluid bed dryer. Product inherent viscosity was 0.68 dL/g and combined phthalyl content was 34.9%.

EXAMPLE 2

Product is prepared as in Example 1 except that 189 g of sodium chlorate (equivalent to a concentration of 1.4%) is added to the mixer immediately after the acetic anhydride addition. Product inherent viscosity was 0.53 dL/g and combined phthalyl content was 35.4%.

EXAMPLE 3

Product is prepared as in Example 1 except that 63 g of sodium chlorate (equivalent to a concentration of 0.5%) is added immediately after the acetic anhydride addition. Product inherent viscosity was 0.59 dL/g and combined phthalyl content was 34.3%.

The examples in Table 2 were prepared in a manner similar to Example 1 above and further illustrate the lower solution viscosity of the cellulose acetate phthalate of our invention.

TABLE VII

Effect of Sodium Chlorate on Cellulose Acetate Phthalate Solution Viscosity

| Reference No. | NaClO3 Conc. (%) | Reaction Time (hr.) | Reaction Temp. (C.) | Inherent Viscosity (dL/g) | Combined Phthalyl (%) |
|---|---|---|---|---|---|
| A | 0.00 | 4.0 | 82 | 0.68 | 35.3 |
| B | 0.25 | 3.0 | 76 | 0.66 | 34.3 |
| C | 0.50 | 2.0 | 82 | 0.64 | 34.4 |
| D | 0.50 | 4.0 | 82 | 0.56 | 34.9 |
| E | 4.04 | 4.0 | 82 | 0.47 | 34.9 |
| F | 2.11 | 4.0 | 82 | 0.52 | 35.2 |
| G | 3.56 | 4.0 | 83 | 0.41 | 35.2 |

We claim:

1. An enteric coating composition comprising (a) cellulose acetate phthalate having an inherent viscosity of about 0.2 to 0.6 dL/g, measured at 25° C. in a (60/40 by weight) mixture of phenol/tetrachloroethane at a concentration of 0.5 g/100 mL and having phthalyl values of 30 to 40%; and (b) an organic solvent.

2. The composition of claim 1, wherein the inherent viscosity is about 0.30 to 0.48 dL/g.

3. The composition of claim 1, wherein the inherent viscosity is about 0.35 to 0.45 dL/g.

4. An enteric coating composition consisting essentially of (a) a binder component consisting essentially of cellulose acetate phthalate having an inherent viscosity of about 0.2 to 0.6 dL/g, measured at 25° C. in a (60/40 by weight) mixture of phenol/tetrachloroethane at a concentration of 0.5 g/100 mL and having phthalyl values of 30 to 40%;

(b) an organic solvent; and (c) one or more additives selected from the group consisting of plasticizers; annealing agents, pharmaceutical clays; surfactants; and thickening agents.

5. The composition of claim 4, wherein the inherent viscosity is about 0.30 to 0.48 dL/g.

6. The composition of claim 4, wherein the inherent viscosity is about 0.35 to 0.45 dL/g.

7. An active ingredient or medicament in granular or tabletted form, coated with an enteric coating composition comprising cellulose acetate phthalate having an inherent viscosity of about 0.2 to 0.6 dL/g, measured at 25° C. in a (60/40 by weight) mixture of phenol/tetrachloroethane at a concentration of 0.5 g/100 mL and having phthalyl values of 30 to 40%.

8. The composition of claim 7, wherein the inherent viscosity is about 0.30 to 0.48 dL/g.

9. The composition of claim 7, wherein the inherent viscosity is about 0.35 to 0.45 dL/g.

* * * * *